(12) United States Patent
McNeff et al.

(10) Patent No.: US 10,849,976 B2
(45) Date of Patent: Dec. 1, 2020

(54) COMPOSITIONS AND METHODS FOR PROTECTING SAPONIN ACTIVITY

(71) Applicant: SarTec Corporation, Anoka, MN (US)

(72) Inventors: Clayton V. McNeff, Andover, MN (US); Larry C. McNeff, Anoka, MN (US); Sandra Maria Hinz, Plymouth, MN (US); Peter G. Greuel, Anoka, MN (US)

(73) Assignee: SarTec Corporation, Anoka, MN (US)

( * ) Notice: Subject to any disclaimer, the term of this patent is extended or adjusted under 35 U.S.C. 154(b) by 354 days.

(21) Appl. No.: 15/448,808

(22) Filed: Mar. 3, 2017

(65) Prior Publication Data

US 2017/0258910 A1    Sep. 14, 2017

Related U.S. Application Data

(60) Provisional application No. 62/305,800, filed on Mar. 9, 2016.

(51) Int. Cl.

| | |
|---|---|
| *A61K 36/896* | (2006.01) |
| *A61K 47/02* | (2006.01) |
| *A23K 50/10* | (2016.01) |
| *A23K 10/30* | (2016.01) |
| *A23K 20/22* | (2016.01) |
| *A23K 20/163* | (2016.01) |
| *A23K 20/20* | (2016.01) |
| *A23K 20/10* | (2016.01) |
| *A61K 31/704* | (2006.01) |
| *A61K 36/185* | (2006.01) |
| *A61K 36/88* | (2006.01) |

(52) U.S. Cl.
CPC ............ *A61K 47/02* (2013.01); *A23K 10/30* (2016.05); *A23K 20/10* (2016.05); *A23K 20/163* (2016.05); *A23K 20/20* (2016.05); *A23K 20/22* (2016.05); *A23K 50/10* (2016.05); *A61K 31/704* (2013.01); *A61K 36/185* (2013.01); *A61K 36/88* (2013.01)

(58) Field of Classification Search
None
See application file for complete search history.

(56) References Cited

U.S. PATENT DOCUMENTS

| | | | |
|---|---|---|---|
| 3,150,979 A * | 9/1964 | Ensley | A23K 50/10 424/115 |
| 5,139,779 A | 8/1992 | McNeff | |
| 5,240,727 A | 8/1993 | McNeff | |
| 5,279,838 A | 1/1994 | McNeff | |
| 5,518,750 A | 5/1996 | McNeff | |
| 7,416,742 B2 | 8/2008 | McNeff et al. | |
| 7,544,376 B2 | 6/2009 | McNeff et al. | |
| 7,641,920 B2 | 1/2010 | Taylor, Jr. et al. | |
| 8,043,633 B2 | 10/2011 | McNeff et al. | |
| 8,048,458 B2 | 11/2011 | McNeff et al. | |
| 9,107,941 B2 | 8/2015 | McNeff et al. | |
| 2010/0034901 A1 * | 2/2010 | Johnson, Jr. | A61K 31/375 424/657 |
| 2010/0143508 A1 * | 6/2010 | Scarbrough | A61K 31/015 424/725 |

FOREIGN PATENT DOCUMENTS

| | | | |
|---|---|---|---|
| CN | 102078451 A * | 6/2011 | |
| CN | 104829305 A * | 8/2015 | |
| JP | 2006061092 A * | 3/2006 | |

* cited by examiner

*Primary Examiner* — Ralph J Gitomer
(74) *Attorney, Agent, or Firm* — Pauly, DeVries Smith & Deffner LLC

(57) ABSTRACT

The invention is related to compositions including saponins and saponin-protective agents and related methods. In an embodiment, a composition is included herein. The composition can specifically include a saponin composition comprising saponins and a saponin-protective agent, wherein the saponin-protective agent prevents deglycosylation of the saponins in an aqueous environment containing glycosidase enzymes. Other embodiments are included herein.

16 Claims, 2 Drawing Sheets

COMPOSITIONS AND METHODS FOR PROTECTING SAPONIN ACTIVITY

This application claims the benefit of U.S. Provisional Application No. 62/305,800, filed Mar. 9, 2016, the content of which is herein incorporated by reference in its entirety.

FIELD OF THE INVENTION

The invention is related to compositions including saponins and saponin-protective agents and related methods.

BACKGROUND OF THE INVENTION

Saponins are naturally occurring plant compounds. Saponin containing compositions have been usefully applied for many different applications. As an example, saponin containing compositions have been shown to significantly reduce methane production when fed to ruminants. This is thought to occur by the saponins forming an irreversible complex with cholesterol in the protozoa membrane and causing lysis. There are many other applications for saponins.

SUMMARY OF THE INVENTION

The invention is related to compositions including saponins and saponin-protective agents and related methods. In an embodiment, a composition is included herein. The composition can specifically include a saponin composition comprising saponins and a saponin-protective agent, wherein the saponin-protective agent prevents deglycosylation of the saponins in an aqueous environment containing glycosidase enzymes.

In an embodiment, a method of processing animal feed is included herein. The method can include contacting an animal feed material with a composition, the composition comprising a saponin composition comprising saponins and a saponin-protective agent, wherein the saponin-protective agent prevents deglycosylation of the saponins in an aqueous environment containing glycosidase enzymes.

In an embodiment, a method of treating an animal to reduce methane emissions is included. The method can include administering to an animal an effective amount of a composition, the composition comprising a saponin composition comprising saponins and a saponin-protective agent, wherein the saponin-protective agent prevents deglycosylation of the saponins in an aqueous environment containing glycosidase enzymes.

In an embodiment, a method of treating an animal to reduce protozoal counts is included. The method can include administering to an animal an effective amount of a composition, the composition comprising a saponin composition comprising saponins; and a saponin-protective agent, wherein the saponin-protective agent prevents deglycosylation of the saponins in an aqueous environment containing glycosidase enzymes.

The above summary of the present invention is not intended to describe each discussed embodiment of the present invention. This is the purpose of the detailed description that follows.

BRIEF DESCRIPTION OF THE FIGURES

Aspects may be more completely understood in connection with the following drawings, in which.

Figure 1:
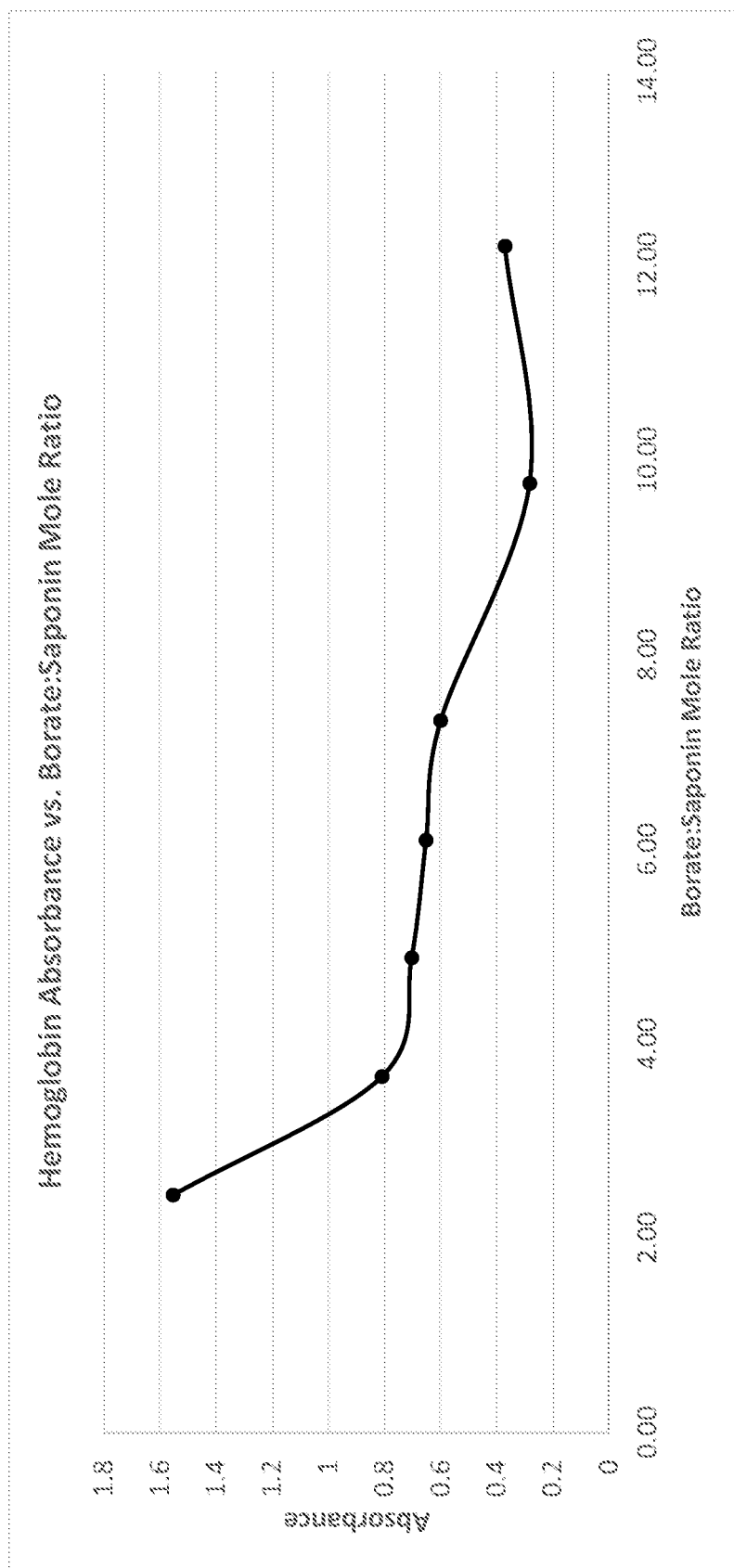
FIG. 1 is a graph showing hemoglobin absorbance (at 417 nm) versus the borate to saponin mole ratio (each mixture was diluted 10-fold to obtain these values).

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION OF THE INVENTION

Saponins are versatile molecules with many different applications. However, it has been discovered that they are inactivated (or their activity is reduced) in certain environments. This is believed to be a result of enzymatic degradation. Compositions used with embodiments herein can include saponins in combination with a saponin-protective agent. The saponin-protective agent can prevent deglycosylation of the saponins in an aqueous environment containing glycosidase enzymes. Normally, the glycosidase enzymes will function to cleave glycosidic bonds of the saponins, but the saponin-protective agent can be effective to prevent this from happening or reduce the incidence of this happening.

In some embodiments, compositions included herein can be mixed in with animal feed, thereby simplifying dosing. In this manner, the composition can act as a feed conditioning agent. Therefore, in an embodiment, the invention includes a feed conditioning composition including a saponin composition comprising saponins; and a saponin-protective agent, wherein the saponin-protective agent prevents deglycosylation of the saponins in an aqueous environment containing glycosidase enzymes. Saponins, described more fully below, have various beneficial dietary properties when fed to animals. Some embodiments of compositions herein can include an amount of saponins. For example, in an embodiment, the invention includes a feed conditioning composition including a saponin composition comprising saponins and a saponin-protective agent, wherein the saponin-protective agent prevents deglycosylation of the saponins in an aqueous environment containing glycosidase enzymes.

Compositions included with embodiments herein can be formulated in various ways. For example compositions herein can be formulated as a liquid, slurry, dry powder, dry granular mix, paste, pellets, block, or the like. Compositions may be administered to an animal as a pill, a bolus, or a liquid drench.

In accordance with embodiments included herein, compositions including a saponin composition comprising saponins and a saponin-protective agent can be administered to an animal along with the animal's feed ration. For example, a composition, such as a liquid composition, can be mixed in with an animal's feed ration. In some embodiments, a composition, such as a liquid composition, can be mixed in with an animal's water.

Saponins

Various compositions herein can include saponins and/or saponin compositions. Saponins are natural plant surfactants that occur in over 500 different plant species belonging to some 80 different families. They are generally recognized by their strong foaming action when placed in water, which has made them especially useful in the manufacture of foods, beverages, shampoos, wetting agents and pharmaceuticals.

Saponins are classified as surfactants because they have both lipophilic and hydrophilic "regions". Thus, the surfactant activity of saponins is a result of both fat-soluble and water-soluble moieties in the same molecule. The lipophilic region may be a steroid, triterpene, or alkaloid, and is termed a sapogenin. The hydrophilic "region" contains one or more water-soluble carbohydrate side chains. The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration. Saponins have an antiprotozoal activity attributed to the saponin's ability to interact with cholesterol in protozoal cell membranes and cause cell lysis.

Saponins useful in the present invention can be extracted from plants of the family: Lillaecae, genus: *Yucca*, such as *Yucca schidigera*. *Yucca* derived saponins generally have steroidal sapogenins. Sarsasapogenin is the major sapogenin found in the *Yucca schidigera* plant. Saponins useful in the present invention can also be extracted from plants of the family: Amaryllidaccae, genus: *Agave*, which grows extensively in the southwestern United States and in Mexico. Additional sources of saponins can include extracts of soybeans, fenugreek, peas, tea, yams, sugar beets, alfalfa, asparagus, aloe, vanilla, zhimu, *Sapindus saponaria*, citrus fruits (limonoid saponins) as well as from *Quillaja saponaria* bark. Saponins can be extracted from plant materials in accordance with techniques well-known by those of skill in the art.

The typical saponin content that naturally occurs in *Yucca* plants is from 0.1-2% saponins by weight. *Yucca* extracts can be derived by extracting *yucca* powder with an aqueous solution that may or may not contain some fraction of organic solvent such as methanol, ethanol, propanol, butanol, or the like.

Commercially available *Yucca* extracts can have total solids content usually in the range from 5-50%. The saponin content of a typical 50 brix (50% solids by weight) *yucca* extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) *yucca* extract is usually in the range of about 5-20% saponins content by weight as measured by the butanol extract method.

In an embodiment, the composition can include at least 0.1% by weight saponins as measured by HPLC. In an embodiment, the composition can include at least 0.5% by weight saponins as measured by HPLC. In an embodiment, the composition can include at least 1.0% by weight saponins as measured by HPLC. In an embodiment, the composition can include at least 2.0% by weight saponins as measured by HPLC.

Saponin-Protective Agents

Compositions used with embodiments herein can include a saponin-protective agent. The saponin-protective agent can prevent deglycosylation of the saponins in an aqueous environment containing glycosidase enzymes. Normally, the glycosidase enzymes will function to cleave glycosidic bonds of the saponins, but the saponin-protective agent can be effective to prevent this from happening or reduce the incidence of this happening. In some embodiments, the saponin-protective agent can include comprising a metal salt. In some embodiments, the saponin-protective agent can include a metal borate salt. In some embodiments, the saponin-protective agent can include sodium borate, sodium tetraborate, or disodium tetraborate. In some embodiments, the saponin-protective agent can include any compound generating borate ions ($B_4O_7^{2-}$) when put into an aqueous solution.

The saponin-protective agent and the saponins can be in a molar ratio of 20:1 to 1:20. The saponin-protective agent and the saponins can be in a molar ratio of 12:1 to 1:12. The saponin-protective agent and the saponins can be in a molar ratio of 4:1 to 1:4. The saponin-protective agent and the saponins can be in a molar ratio of 2:1 to 1:2.

In some embodiments, the saponin-protective agent and the saponins can be in a molar ratio of 12:1 to 1:1. In some embodiments, the saponin-protective agent and the saponins can be in a molar ratio of 12:1 to 2:1. In some embodiments, the saponin-protective agent and the saponins can be in a molar ratio of 12:1 to 3:1. In some embodiments, the saponin-protective agent and the saponins can be in a molar ratio of 6:1 to 1:1. In some embodiments, the saponin-protective agent and the saponins can be in a molar ratio of 6:1 to 2:1. In some embodiments, the saponin-protective agent and the saponins can be in a molar ratio of 4:1 to 1:1. In some embodiments, the saponin-protective agent and the saponins can be in a molar ratio of 4:1 to 2:1.

In some embodiments, the saponin-protective agent and the saponins are in a weight ratio of about 1:5 to 1:50. In some embodiments, the saponin-protective agent and the saponins are in a weight ratio of about 1:10 to 1:30.

In some embodiments, the composition can include at least about 0.1, 0.5, 1.0, 2.0, 4.0, 6.0, 8.0, 10, 15 or 20% by weight of the saponin-protective agent. In some embodiments the composition can include less than about 25, 20, 15, 10, 8.0, 5.0 or 2.0% by weight of the saponin-protective agent. In some embodiments, the amount of the saponin-protective agent can be in a range wherein any of the foregoing numbers can serve as the upper or lower bound of the range.

In various embodiments, the saponin-protective agent can be mixed with the saponins before administration to an animal. In various embodiments, the saponin-protective agent can be mixed with the saponins before the saponins are exposed to an aqueous environment containing glycosidase enzymes, such as in vivo within a subject. As such, in some embodiments, the saponin-protective agent and the saponins are administered as a single composition.

It will be appreciated that methods and compositions of the invention can be used for the treatment of animals, including bovine, fowl, porcine, ovine, and equine species. By way of example, the methods and compositions of the invention can be used for the treatment of cattle, chickens, turkeys, ducks, quail, geese, pigs, and sheep. In a specific embodiment, the methods and compositions of the invention can be used for the treatment of ruminants.

For example, in an embodiment, a method of treating an animal to reduce methane emissions is included. The method can include administering to an animal an effective amount of a composition, the composition comprising a saponin composition comprising saponins and a saponin-protective agent, wherein the saponin-protective agent prevents deglycosylation of the saponins in an aqueous environment containing glycosidase enzymes.

As another example, in an embodiment, a method of treating an animal to reduce protozoal counts is included. The method can include administering to an animal an effective amount of a composition, the composition comprising a saponin composition comprising saponins; and a saponin-protective agent, wherein the saponin-protective agent prevents deglycosylation of the saponins in an aqueous environment containing glycosidase enzymes.

It will be appreciated that compositions in accordance with embodiments herein can include various additives. By way of example, compositions can also include additives such as water, propylene glycol, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey, amongst others.

Aspects of the present invention may be better understood with reference to the following examples. These examples are intended to be representative of specific embodiments of the invention, and are not intended as limiting the scope of the invention.

Animal Feed Materials

In an embodiment, the invention includes a method of processing animal feed including contacting an animal feed material with a composition including a saponin composition comprising saponins and a saponin-protective agent. Embodiments also include animal feed compositions processed according to such methods. By adding the composition to the animal feed, dosing can be simplified as the composition will reach the rumen along with the feed.

It will be appreciated that animal feed materials can include many different components such as, but not limited to, alfalfa hay, alfalfa haylage, almond hulls, apple components, rolled barley, barley malt sprouts, barley silage, bermuda grass, blood meal, bluegrass, brome, canary grass, canola seed, canola meal, chocolate byproduct, dried citrus pulp, clover, sudangrass hay, dry-rolled corn, tempered-rolled corn, steam-flaked corn, ground shelled corn, cracked corn, hominy feed, corn gluten feed, corn silage, wet brewer's grain, dry brewer's grain, distillers grains (dried and wet), stillage, soybean meal, soybean seeds, soybean hulls, sunflower meal, sunflower oil, sunflower seeds, tomato products, wheat bran, rolled wheat, wheat hay, wheat middlings, wheat silage, whey, fescue, fish byproducts, hay, legumes, linseed, meat meal, meat and bone meal, rolled oats, oat hay, oat silage, orchard grass, peanut meal, potato byproduct meal, rice bran, rye, safflower, dry rolled sorghum, steam-flaked sorghum, sorghum silage, soybean hulls, whole cottonseed, cottonseed hulls, cottonseed meal, sugar beet pulp, dehydrated beet pulp, bakery waste, cottonseed meal, yellow grease, white grease, vegetable oil, tallow, water, hydrolyzed feather meal, cane molasses, sugar beat molasses, and the like, and combinations thereof.

In some embodiments, the animal feed material can specifically include byproducts of ethanol production. For example in some embodiments, the animal feed material can specifically include distillers dried grains, distillers wet grains, and/or stillage.

Aspects may be better understood with reference to the following examples. These examples are intended to be representative of specific embodiments, but are not intended as limiting the overall scope of embodiments herein.

EXAMPLES

Example 1—Saponin Protection with Borate

Saponins are well known for their ability to lyse red blood cells (RBCs). RBCs contain hemoglobin enzymes with heme groups surrounding iron atoms that give a deep, rich red color to blood. If a blood solution is centrifuged, the RBCs gravitate to the bottom of the centrifuge tube and the supernatant solution becomes nearly colorless as most of the color lies in the chromophore ability of the iron atoms within the RBCs. However, once an RBC is lysed the hemoglobin leaves the confines of the cell and remains dispersed. Even after centrifugation the supernatant solution of lysed RBCs, has a deep red color.

While saponin-protective agents herein can protect the saponin from degradation by glycosidase enzymes, such protective agents can also block the saponin from lysing RBCs. Therefore, evaluating the effect of protective agents on saponin RBC lysing activity can be used to show the efficacy of the saponin-protective agent.

In addition, a saponin molecule has a few to several glucose units bonded to it, depending on the exact plant from which the saponin is extracted. Each glucose unit bonded to the saponin may have up to four more hydroxy (—OH) groups attached and pointing outward from the glucose ring into the water solution. Glucose concentrations can be measured by an assay that depends on glucose oxidase acting upon glucose. However, glucose oxidase is prevented from acting upon glucose if borate is effectively bound to glucose. Thus, observing a declining amount of glucose as measured using a glucose oxidase based assay is indicative of borate binding to glucose, which in turn, serves as another indication of the efficacy of the saponin-protective agent.

Aqueous solutions of saline, saponin, borate, and glucose were used in this study. All aqueous solutions were prepared using purified reverse osmosis water. A 0.9% by weight aqueous saline solution of sodium chloride (NaCl) (Sigma-Aldrich Corp., St. Louis, Mo.) was prepared. A 2% by weight aqueous saponin solution was prepared using saponin from *quillaja* bark (Sigma-Aldrich Corp., St. Louis, Mo.). A 2.0% by weight borate solution was prepared using commercially available borax (sodium borate).

Bovine blood (Lampire Biological Laboratories, Pipersville, Pa.), containing the manufacturer's standard anticoagulant, was cold-shipped overnight and stored at 4° C. to retain its properties (for up to two weeks). All experiments were run within 3 days of receiving the bovine blood. A standard glucose solution was prepared using glucose (Sigma-Aldrich Corp., St. Louis, Mo.). A Beckman Du-65 UV/VIS Spectrometer (Beckman Coulter, Inc., Brea, Calif.) and a OneTouch® Ultra 2 (LifeScan, Inc., Wayne, Pa.) blood glucose meter were used for hemoglobin and glucose determinations, respectively.

Red blood cell (RBC) lysis solutions (e.g., containing no saponin-protective agent) were prepared using saline, saponin solution, and bovine blood. No borate was added to these solutions. Predetermined volumes of saponin and saline for each solution shown in Table 1 were mixed together and then bovine blood was added to each mixture. The mixtures were put into individual 10 mL polyethylene centrifuge vials, capped, and then shaken for 30 sec. The vials were centrifuged at 2,000 rpm for 3 min. A glass pipette was used to carefully suction off each supernatant solution and place it into a 1 cm glass cuvette. Each cuvette was individually placed into the UV/VIS spectrometer and solution absorbance values were measured for each solution at 417 nm, 547 nm, and 575 nm wavelengths (these are known wavelengths for local maximum absorbance peaks of hemoglobin). Additionally, 1 mL of each supernatant solution was pipetted into a clean glass vial and diluted to 10 mL with saline solution. Each dilution was mixed and again put into a 1 cm cuvette and the absorbance values were measured at the same wavelengths. Before each absorbance value was taken, a calibration was performed with reverse osmosis water in a cuvette as a blank at each chosen wavelength.

Non-lysing RBC solutions (e.g., containing a saponin-protective agent) were prepared with saline, borate solution, saponin solution, and bovine blood. Predetermined volumes of saline and borate for each solution shown in Table 1 were mixed together in individual 10 mL centrifuge vials and then the predetermined volume of each saponin solution was added to each vial and mixed. Finally, the bovine blood was added. Each vial was capped and the mixtures were shaken for 30 sec before centrifugation at 2,000 rpm for 3 min. Each supernatant was diluted 10-fold in saline. Both the non-diluted and 10-fold diluted supernatants were placed into 1 cm glass cuvettes and their absorbance values were measured at 417 nm, 547 nm, and 575 nm wavelengths. Table 1 lists the absorbance values determined for the diluted solutions at 417 nm, chosen because as the most sensitive absorbance peak for hemoglobin. The non-diluted mixture values are not reported, as they all gave absorbance values greater than 3.00 and hence beyond the limits of Beer's Law. Note that the sample containing no borate ("lysed sample") was diluted to a 50-fold total dilution of the original mixed solution to give an acceptable absorbance value.

TABLE 1

The solution volumes that were mixed and the resulting absorbance values of the supernatant solution after centrifugation.

| Solution Volumes Added: | | | | Absorbance Values | Borate:Saponin |
|---|---|---|---|---|---|
| Borate | Saponin | Saline | Blood | (417 nm) | Molar Ratios |
| 1.00 | 0.20 | 2.80 | 1.00 | 0.371 | 12.20:1 |
| 0.80 | 0.20 | 3.00 | 1.00 | 0.283 | 9.76:1 |
| 0.60 | 0.20 | 3.20 | 1.00 | 0.600 | 7.32:1 |
| 0.50 | 0.20 | 3.30 | 1.00 | 0.652 | 6.09:1 |
| 0.40 | 0.20 | 3.40 | 1.00 | 0.704 | 4.88:1 |
| 0.30 | 0.20 | 3.50 | 1.00 | 0.809 | 3.66:1 |
| 0.20 | 0.20 | 3.60 | 1.00 | 1.554 | 2.44:1 |
| 0.00 | 0.20 | 3.80 | 1.00 | *1.831 | 0 |

(*a 50-fold total dilution for this value.)

For the experimental mixtures, the borate volume was varied while the blood and saponin volumes, as well as the total volume mixed were held constant through varying the saline volume.

A standard glucose solution was prepared by weighing about 0.9 g of glucose and 0.450 g of NaCl into a 500.0 mL volumetric flask. Reverse osmosis water was added while mixing the reagents to reach the 500 mL total volume. Next, a 40.0 mL portion of the standard glucose solution was added to a 50 mL vial and 0.106 g of sodium borate was successively added resulting in a molar ratio of borate:glucose in a range of 1:1 to 6:1. Glucose levels were measured using a OneTouch Ultra 2 blood glucose meter. Table 2 shows the glucose levels measured for each solution.

TABLE 2

The amounts of sodium borate added to a standard glucose solution, the borate:glucose molar ratio, and the glucose meter readings given for the solutions.

| Amount of Sodium Borate Added | Borate:Glucose Molar Ratio | Glucose Meter Reading |
|---|---|---|
| 0 | 0 | 185 mg/dL |
| 0.106 | 1:1 | 106 mg/Dl |
| 0.212 | 2:1 | 38 mg/Dl |
| 0.318 | 3:1 | "Low Glucose < 20 mg/dL" |
| 0.636 | 6:1 | "Error 4" |
| 0 | 0:1 | 186 mg/dL |

The glucose level for the standard glucose/saline solution was taken both before and after the borate-containing glucose solutions were measured for glucose concentration.

Figure 2:
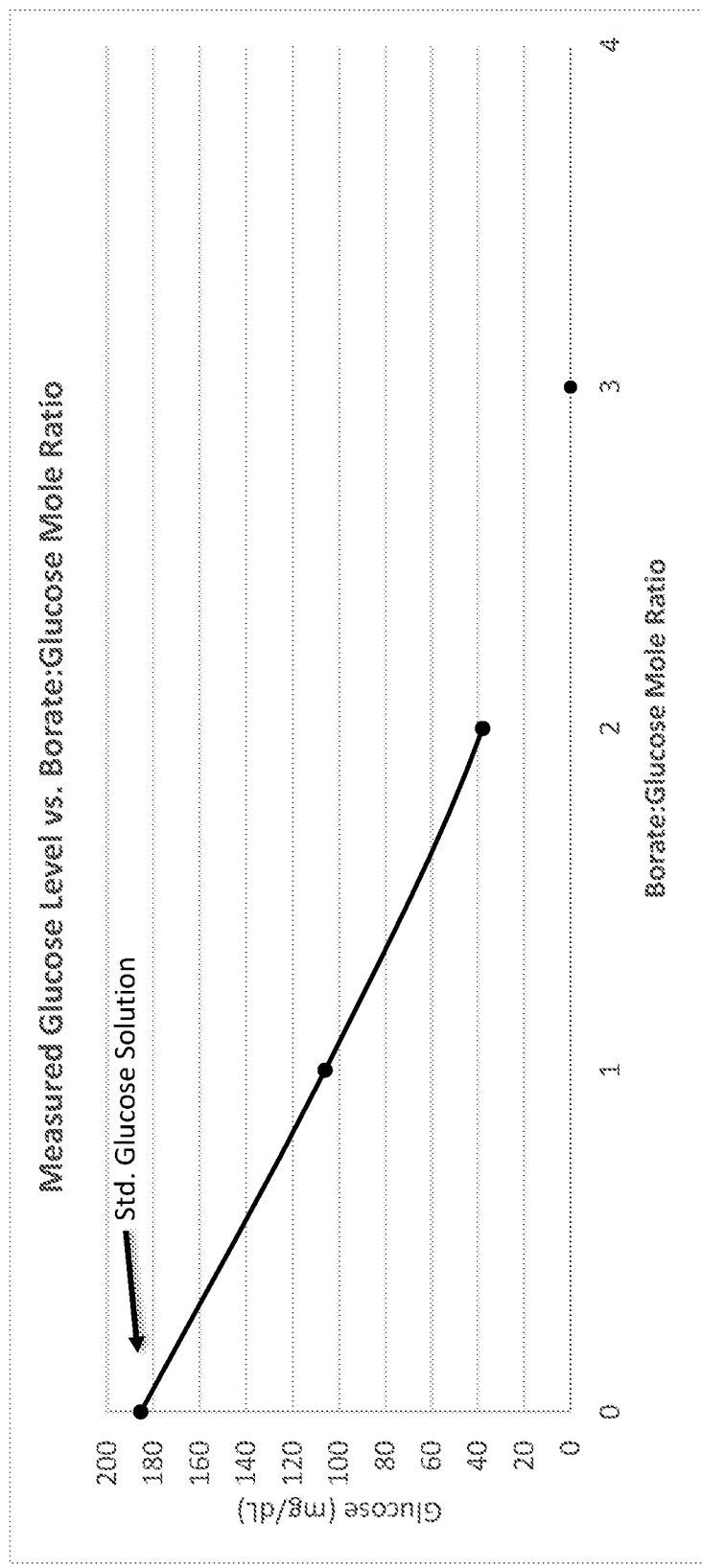
FIG. 2 is a graph showing glucose levels measured, in mg/dL units, versus the borate:glucose mole ratios obtained by adding sodium borate to a portion of the standard glucose solution.

Using average molecular weights for the *quillaja* bark saponin of 929.1 grams per mol (g/mol) and for sodium borate of 381.4 g/mol, the molar ratios of borate to saponin could be determined. Using equal volumes of the same weight percent solutions (2% by weight) the borate:saponin molar ratio was 2.44:1. The molar ratio was varied from 0:1 (no borate added) up to 12.20:1. FIG. 1 shows a plot of the absorbance values of the supernatants (at 417 nm) versus the molar ratio of borate to saponin. FIG. 2 shows a plot of the glucose levels measured in mg/dL units, versus the borate:glucose molar ratios obtained by adding sodium borate to the standard glucose solution.

The results in FIG. 1 show that an increasing borate to saponin molar ratio resulted in a decrease in the concentration of hemoglobin found in the supernatant. The results show that as the borate:saponin molar ratio increased, the hemoglobin concentration in the supernatant decreased until the 9.76:1 molar ratio was reached. A slight increase in hemoglobin concentration was reported at the 12.2:1 molar ratio, which is attributed to experimental error of the actual concentration of hemoglobin in the blood aliquots taken.

The results in FIG. 2 show an approximately linear decrease in the free glucose concentration as borate concentration increases. Note that the plot was not extrapolated to the 3:1 data point because of the inability of the glucose monitor to present a numerical readout (likely due to limitations in the ability of the monitor to determine such low free glucose concentrations). Thus, glucose is effectively entirely protected from oxidation by glucose oxidase at a 3:1 borate:glucose molar ratio (the working component in the strips is glucose oxidase enzyme). The 6:1 borate:glucose molar ratio data point similarly left off the graph.

Taken together, the results of this example show that borate can serve as an effective saponin-protective agent.

The invention claimed is:

1. An animal feed conditioning composition comprising:
   a saponin composition comprising saponins derived from the family Liliaceae or the family Amaryllidaceae; and
   a saponin-protective agent comprising a borate group, wherein the saponin-protective agent prevents deglycosylation of the saponins in an aqueous environment containing glycosidase enzymes.

2. The composition of claim 1, the saponin-protective agent comprising a metal salt.

3. The composition of claim 2, the metal salt comprising a metal borate salt.

4. The composition of claim 2, the metal salt comprising sodium borate.

5. The composition of claim 1, wherein the saponin-protective agent and the saponins are in a molar ratio of 12:1 to 1:12.

6. The composition of claim 1, wherein the saponin-protective agent and the saponins are in a molar ratio of 4:1 to 1:1.

7. The composition of claim 1, wherein the saponin-protective agent and the saponins are in a weight ratio of about 1:10 to 1:30.

8. The composition of claim 1, comprising at least about 0.1% by weight of the saponin-protective agent.

9. The composition of claim 1, comprising at least about 0.1% by weight of saponins.

10. The composition of claim 1, the saponin composition is derived from a plant extract.

11. The composition of claim 10, the plant extract comprising *yucca* extract.

12. The composition of claim 1, the saponin composition comprising sarsaponins.

13. The composition of claim 1, the saponin composition is formulated as a liquid composition.

14. The composition of claim 1, further is formulated as a liquid, a slurry, a dry powder, a dry granular mix, a paste, a pellet, or a block.

15. An animal feed conditioning composition comprising:

a saponin composition comprising saponins;

a saponin-protective agent comprising a borate group, wherein the saponin-protective agent prevents deglycosylation of the saponins in an aqueous environment containing glycosidase enzymes; and at least one additive selected from the group consisting of propylene glycol, Vitamin E, Vitamin A Propionate, Vitamin A Palmitate, Vitamin B1, Vitamin B2, Vitamin B6, Vitamin B12, D-Activated Animal Sterol, yeast components, dried egg solids, dried casein, and dried whey.

16. The composition of claim 1, wherein the saponin-protective agent and the saponins are in a molar ratio of about 2:1 to 1:2.

* * * * *